US007566448B2

(12) United States Patent
Becker et al.

(10) Patent No.: US 7,566,448 B2
(45) Date of Patent: Jul. 28, 2009

(54) REDUCED AEROSOL GENERATING FORMULATIONS

(75) Inventors: Nathaniel T. Becker, Hillsborough, CA (US); Herbert B. Scher, Moraga, CA (US); Deborah S. Winetzky, Foster City, CA (US)

(73) Assignee: Genencor International, Inc., Palo Alto, CA (US)

( * ) Notice: Subject to any disclaimer, the term of this patent is extended or adjusted under 35 U.S.C. 154(b) by 356 days.

(21) Appl. No.: 10/626,125

(22) Filed: Jul. 23, 2003

(65) Prior Publication Data

US 2004/0138079 A1    Jul. 15, 2004

Related U.S. Application Data

(60) Provisional application No. 60/399,600, filed on Jul. 30, 2002, provisional application No. 60/426,714, filed on Nov. 15, 2002, provisional application No. 60/433,413, filed on Dec. 13, 2002, provisional application No. 60/454,237, filed on Mar. 12, 2003.

(51) Int. Cl.
    *A61K 38/48*    (2006.01)
(52) U.S. Cl. .................................. 424/94.63
(58) Field of Classification Search ................ 424/400, 424/486, 46, 47, 70.1, 70.16, 94.1, 94.6, 424/94.63; 435/183, 187, 189, 195, 212; 510/391, 130, 279, 475
    See application file for complete search history.

(56) References Cited

U.S. PATENT DOCUMENTS

| | | | |
|---|---|---|---|
| 4,310,434 A | | 1/1982 | Choy et al. |
| 4,407,788 A | * | 10/1983 | Kiozpeoplou ................ 424/49 |
| 4,421,769 A | | 12/1983 | Dixon et al. |
| 4,760,025 A | | 7/1988 | Estell et al. |
| 4,935,224 A | | 6/1990 | Russo et al. |
| 5,068,099 A | * | 11/1991 | Sramek ........................ 424/47 |
| 5,133,968 A | | 7/1992 | Nakayama et al. |
| 5,185,258 A | | 2/1993 | Caldwell et al. |
| 5,204,015 A | | 4/1993 | Caldwell et al. |
| RE34,606 E | | 5/1994 | Estell et al. |
| 5,340,581 A | * | 8/1994 | Tseng et al. ................ 424/401 |
| 5,364,551 A | * | 11/1994 | Lentsch et al. ............. 510/100 |
| 5,441,882 A | | 8/1995 | Estell et al. |
| 5,462,689 A | | 10/1995 | Choy et al. |
| 5,631,217 A | | 5/1997 | Branner et al. |
| 5,665,587 A | | 9/1997 | Aaslyng et al. |
| 5,700,676 A | | 12/1997 | Bott et al. |
| 5,741,694 A | | 4/1998 | Hastrup et al. |
| 5,880,080 A | | 3/1999 | Amory et al. |
| 6,197,567 B1 | | 3/2001 | Aaslyng et al. |
| 6,218,165 B1 | | 4/2001 | Estell et al. |
| 6,235,692 B1 | | 5/2001 | Scoville et al. |
| 6,251,145 B1 | | 6/2001 | De La Mettrie et al. |
| 6,372,842 B1 | | 4/2002 | Grisso et al. |
| 6,379,654 B1 | * | 4/2002 | Gebreselassie et al. ........ 424/50 |
| 6,562,325 B2 | | 5/2003 | Vitale et al. |
| 6,593,288 B2 | * | 7/2003 | Aubay et al. ................ 510/504 |
| 6,835,703 B1 | * | 12/2004 | Cho et al. ................... 510/221 |
| 2003/0175232 A1 | * | 9/2003 | Elliott et al. ............. 424/70.14 |

FOREIGN PATENT DOCUMENTS

| | | |
|---|---|---|
| EP | 0 218 272 B1 | 3/1992 |
| EP | 0 781 839 A1 | 7/1997 |
| EP | 1 240 890 A1 | 9/2002 |
| GB | 2339794 A * | 2/2000 |
| WO | WO 89/06279 | 7/1989 |
| WO | WO 92/10755 | 6/1992 |
| WO | WO 96/23873 | 8/1996 |
| WO | WO98/30682 | 7/1998 |
| WO | WO 99/49056 | 9/1999 |
| WO | WO 00/24372 | 5/2000 |
| WO | WO 01/07579 A3 | 2/2001 |

OTHER PUBLICATIONS

Ferguson et al. "The break-up of fluids in an extensional flow field" J. Non-Newtonian Fluid Mechanics (1992) 44: 37-54.*
The Merck Index. 10th edition. Windholz, editor. (Merck and Company: Rahway, NJ), p. 1444.*
Bachalo, W.D. , "*Spray Diagnostics for the Twenty-First Century*", Atomization and Sprays, vol. 10, pp. 439-474, 2000.
Bergeron, Vance et al,"*Controlling droplet deposition with polymer additives*", Letters to Nature 405 :772-775, 2000.
Bryan, Philip ,"*Protein engineering of subtilisin*", Elsevier Science B.V., Biochimica et Biophysica Acta 1543, 203-222, 2000.
Dexter, R.W. , "*Measurement of Extensional Viscosity of Polymer Solutions and its Effects on Atomization from a Spray Nozzle*", Atomization and Sprays, vol. 6, pp. 167-191, 1996.
Dua, S.K. et al,"*Hygroscopic Growth of Consumer Spray Products*", Aerosol Science and Technology 23 :331-340, 1995.
Fisk, William et al, "*Particle Concentrations and Sizes with Normal and High Efficiency Air Filtration in a Sealed Air-Conditioned Office Building*", Aerosol Science and Technology 32 :527-544, 2000.

(Continued)

*Primary Examiner*—Sandra Saucier
*Assistant Examiner*—Susan Hanley

(57) ABSTRACT

The present invention relates to compositions comprising high molecular weight polymers, particularly polyethylene oxide polymers, wherein the high molecular weight polymer serves as an anti-misting agent to reduce the potential of aerosol generation from a composition when used in a desired environment. The invention further relates to methods of decreasing enzyme exposure from a personal care or cleaning product comprising a high molecular weight polymer.

35 Claims, 2 Drawing Sheets

OTHER PUBLICATIONS

Li, Wei et al, "*Hygroscopicity of Consumer Spray Product Aerosol Particles*", J.Aerosol Sci., vol. 25, No. 7, pp. 1341-1351, 1994.

Priest, Fergus, "*Extracellular Enzyme Synthesis in the Genus Bacillus*", Bacteriological Reviews, p. 711-753, 1977.

Rioboo, R. et al, "*Outcomes from a Drop Impact on Solid Surfaces*", Atomizations and Sprays, vol. 11, pp. 155-165, 2001.

Siezen, Roland et al,"*Homology modelling and protein engineering strategy of subtilases, the family of subtilisn-like serine proteinases*", Protein Engineering vol. 4 No. 7 pp. 719-737, 1991.

Siezen, Roland et al,"*Subtilases : The superfamily of subtilisn-like serine proteases*", Protein Science 6 :501-523, 1997.

Smallwood, Gregory et al, "*Views on the Structure of Transient Diesel Sprays*", Atomization and Sprays, vol. 10, pp. 355-386, 2000.

Stelter, M. et al, "*The Influence of Viscoelastic Fluid Properties on Spray Formation from Flat-Fan and Pressure-Swirl Atomizers*", Atomization and Sprays, vol. 12, pp. 299-327, 2002.

Sudlow, C.A. et al, "*Atomization of Detergent Slurries*", Atomization and Sprays, vol. 4, pp. 629-642, 1994.

Thomas, Walter M., et al., << Acrylic and Methacrylic Acid Polymers, : Wiley-Interscience Publication, John Wiley & Sons, "*Encyclopedia of Polymer Science and Engineering*", vol. 1, A to Amorphous Polymers, pp. 169-211, 1985.

Zhu, H. et al,"*Effects of Polymer Composition and Viscosity on Droplet Size of Recirculated Spray Solutions*", J. agric. Engng Res. 67 :35-45, 1997.

* cited by examiner

REDUCED AEROSOL GENERATING FORMULATIONS

CROSS REFERENCE TO RELATED APPLICATION

This application claims priority to U.S. Provisional Application No. 60/399,600, filed Jul. 30, 2002, to U.S. Provisional Application No. 60/426,714 filed Nov. 15, 2002, to U.S. Provisional Application No. 60/433,413, filed Dec. 13, 2002, and to U.S. Provisional Application No. 60/454,237, filed Mar. 12, 2003.

FIELD OF THE INVENTION

The present invention relates to compositions comprising high molecular weight polymers, particularly polyethylene oxide polymers, wherein the high molecular weight polymer serves as an anti-misting agent to reduce the potential of aerosol generation from a composition when used in a desired environment. Compositions comprising a high molecular weight polymer as an anti-misting agent may be further formulated for use with personal care products and cleaning products to reduce aerosol generation. In one preferred embodiment, the compositions of the invention will be formulated to include an effective amount of an enzyme.

BACKGROUND OF THE INVENTION

It is well known that the dispensing of cleaning and personal care products by spraying or pumping can yield an aerosol or mist, which may potentially cause respiratory distress, sensitization or allergic response in humans, particularly when such products contain a potential allergen, such as a protein. There are two components which contribute to this respiratory distress. The first component is the actual aerosol produced at the site of product supply. When the product is delivered by a finely divided spray the particles are quickly scattered in the air. The second component is product bounce-off or rebound. Once the product is dispensed, the product may bounce off a target material. Target materials may be extremely diverse. For example, skin, a glass surface and a textile may all be target materials. To minimize the risk of respiratory distress or other undesirable biological responses, some products have been formulated to include or exclude various inorganic and organic compounds. Other products have further been formulated and dispensed to adjust particle size of the aerosol.

Choy et al, U.S. Pat. No. 4,310,434 discloses a composition including a polyethylene oxide resin, a surfactant and a water-soluble salt. These ingredients are compressed into a solid cake. The disclosed compositions may comprise 5-20% polyethylene oxide resin, preferably 5-12% resin, with a molecular weight of about 500,000 to about 7,000,000. The resin reduces the tendency for aerosol formation during the flushing of a toilet. The water-soluble salt suppresses the solubility of the resin thereby also suppressing gelation of dissolved resin.

Russo et al., U.S. Pat. No. 4,935,224, teach an aerosol antiperspirant composition including a volatile low-viscosity fluid and a silicone polymer. The silicone polymer is completely dissolved in the composition. The composition avoids dustiness and clogging of the aerosol valve, and upon spraying the composition, product bounce-off is reduced.

Lentsch et al., U.S. Pat. No. 5,364,551, teach reducing the misting of acid or alkaline hard surface cleaners, particularly alkaline oven cleaners, by increasing the mean particle size of the mist droplet dispensed through a spray head to greater than about 170 μm. The compositions include a strong acid or strong base, an organic surfactant, and an organic water soluble polymeric thickener. Various thickeners are disclosed including vinyl polymers. Preferred thickeners for alkaline compositions include xanthan thickeners and preferred thickeners for acid compositions include polyvinyl alcohol thickeners.

Choy et al., U.S. Pat. No. 5,462,689, teach a thickened cleaning composition for a hard surface which reduces the odor of bleach when the composition is sprayed. The spraying of the cleaning composition releases particles which result in the release of bleach odor. These compositions include an aqueous solution of an alkali metal hypochlorite and a thickening system which includes a hexadecyl dialkyl amine oxide and an organic counterion.

Grisso et al., U.S. Pat. No. 6,372,842, disclose aqueous compositions containing a water-soluble synthetic polymer wherein the compositions impart aerosol control in combination with shear stability to a resulting composition when the composition is exposed to a shear rate of 99,000 to 1,000,000 $s^{-1}$ and a shear stress of from 30,000 to 500,000 Pascal. The resulting compositions include agricultural spray compositions, ink compositions, deicing or anti-icing compositions, hydro-metallurgy or electro-winning compositions, cleaner compositions, adhesive compositions, fire extinguishing compositions, organosilane compositions, personal care compositions, latex or other water borne compositions, textile finish compositions water-based hydraulic compositions and dust control compositions. The water-soluble synthetic polymer is formed by the polymerization of an alkyl substituted acrylamide compound and a hydrophilic monomer.

The use of enzymes, especially of microbial origin, has become more and more common in several industries which include, for example, the detergent industry, the personal care industry and the pharmaceutical industry. A critical issue in the use of enzymes in many consumer and industrial applications arises from the fact that enzymes may be potential allergens.

Therefore, a number of strategies have been explored to reduce the immunogenic potential of enzymes and these include improved processes which reduce potential contact by controlling and minimizing workplace concentrations of dust particles or aerosol carrying airborne enzymes, improved granulation processes which reduce the amount of dust or aerosol actually produced from the enzyme product, improved recovery processes to reduce the level of potentially allergenic contaminants in the final product, and even efforts to reduce the allergenicity of the enzyme per se. All of these strategies have had limited success. Accordingly, a need still exists for enzymes to be formulated so as to minimize the risk of sensitization and allergic reaction on the part of individuals who are exposed to enzymes, and particularly in consumer products.

Moreover, since enzymes may be incorporated as an additive into personal care products and cleaning products and upon application of these products aerosols may be created, an accompanying need exists to provide improved formulations and application properties whereby potential aerosol production is reduced from these products.

It is an object of the present invention to provide anti-misting compositions which include a high molecular weight polymer which may be incorporated into personal care and cleaning products whereby the potential for aerosol production is reduced.

It is another object of the present invention to provide anti-misting enzyme compositions which when used in a desired environment or on a target material have a reduced tendency to form aerosol particles.

It is a further object of the present invention to reduce the allergenic potential of an enzyme used in personal care product formulations or in cleaning product formulations.

It is yet a further object of the present invention to reduce misting of shower gels in a shower environment or reduce the misting of laundry pre-spotters.

SUMMARY OF THE INVENTION

In one embodiment the present invention concerns a reduced aerosol generating formulated personal care or cleaning product comprising a high molecular weight polymer and one or more personal care or cleaning product components, wherein said polymer acts as an anti-misting agent and increases the $Dv_{50}$ of the formulated personal care or cleaning product by 10-200% over the $Dv_{50}$ of the corresponding non-formulated personal care or cleaning product.

In another embodiment the present invention concerns a method of reducing aerosol generation from a personal care or cleaning product comprising incorporating into said product an aqueous composition comprising a high molecular weight polymer having a molecular weight from about $0.8 \times 10^6$ to $4.0 \times 10^7$, resulting in a formulated product wherein the $Dv_{50}$ of said formulated product is between 10 to 200% greater than the $Dv_{50}$ of the corresponding non-formulated personal care or cleaning product.

In a further embodiment the invention concerns a method of decreasing enzyme exposure from a personal care product comprising reformulating a personal care product which includes one or more enzymes with an aqueous composition which comprises a polyethylene oxide polymer having a molecular weight of about $0.8 \times 10^6$ to $4.0 \times 10^6$ wherein said polymer acts as an anti-misting agent.

In yet another embodiment the invention concerns an aqueous anti-misting enzyme composition comprising from about $1 \times 10^{-4}$ to 25 wt % of one or more high molecular weight polymers; and from about $1 \times 10^{-3}$ to 25 wt % of an effective amount of one or more enzymes.

In still a further embodiment the invention relates to a shower gel comprising a high molecular weight polymer wherein said polymer has a molecular weight from about $0.8 \times 10^6$ to $4.0 \times 10^7$ and comprises from about 0.0001% to about 10% of the shower gel; a protease comprising about 0.0001% to about 10% of the shower gel; and one or more further personal care product ingredients wherein said shower gel has a $Dv_{50}$ that is 10-200% greater than a corresponding shower gel lacking the high molecular weight polymer.

The invention further relates to a method for producing a reduced aerosol generating composition comprising combining a high molecular weight polymer having a molecular weight of about $0.8 \times 10^6$ to about $4 \times 10^7$ with an enzyme to obtain a polymer/enzyme composition.

Additionally, the invention relates to a method for producing a reduced aerosol generating composition comprising combining a high molecular weight polymer having a molecular weight of about $0.8 \times 10^6$ to about $4 \times 10^7$ with an enzyme to obtain a polymer/enzyme composition; incorporating the polymer/enzyme composition with a personal care or cleaning product composition; and obtaining a formulated personal care or cleaning product composition wherein when said formulated product is used in a desired environment. The generation of aerosols produced by the formulated product is reduced compared to a corresponding non-formulated product.

Another embodiment of the invention relates to a method of reducing the generation of aerosols comprising combining a high molecular weight polymer having a molecular weight of about $0.8 \times 10^6$ to about $4 \times 10^7$ with an enzyme to obtain a polymer/enzyme composition; combining the polymer/enzyme composition with a personal care or cleaning product formulation; and using the formulation in a desired environment wherein the mean particle aerosol size of the formulation is between 65-150 µm.

In still yet another embodiment the invention relates to a method of reducing aerosol generation of a formulation comprising reformulating a personal care formulation or cleaning formulation with a composition comprising a polyethylene oxide polymer having a molecular weight from about $0.8 \times 10^6$ to about $4.0 \times 10^6$ and comprising from about 0.0001% to about 10% of the formulation, wherein the addition of the polymer increases the $Dv_{50}$ of the personal care or cleaning formulation by 10-200% resulting in reduced aerosol generation from the personal care or cleaning formulation.

DETAILED DESCRIPTION OF THE INVENTION

Figure 1:
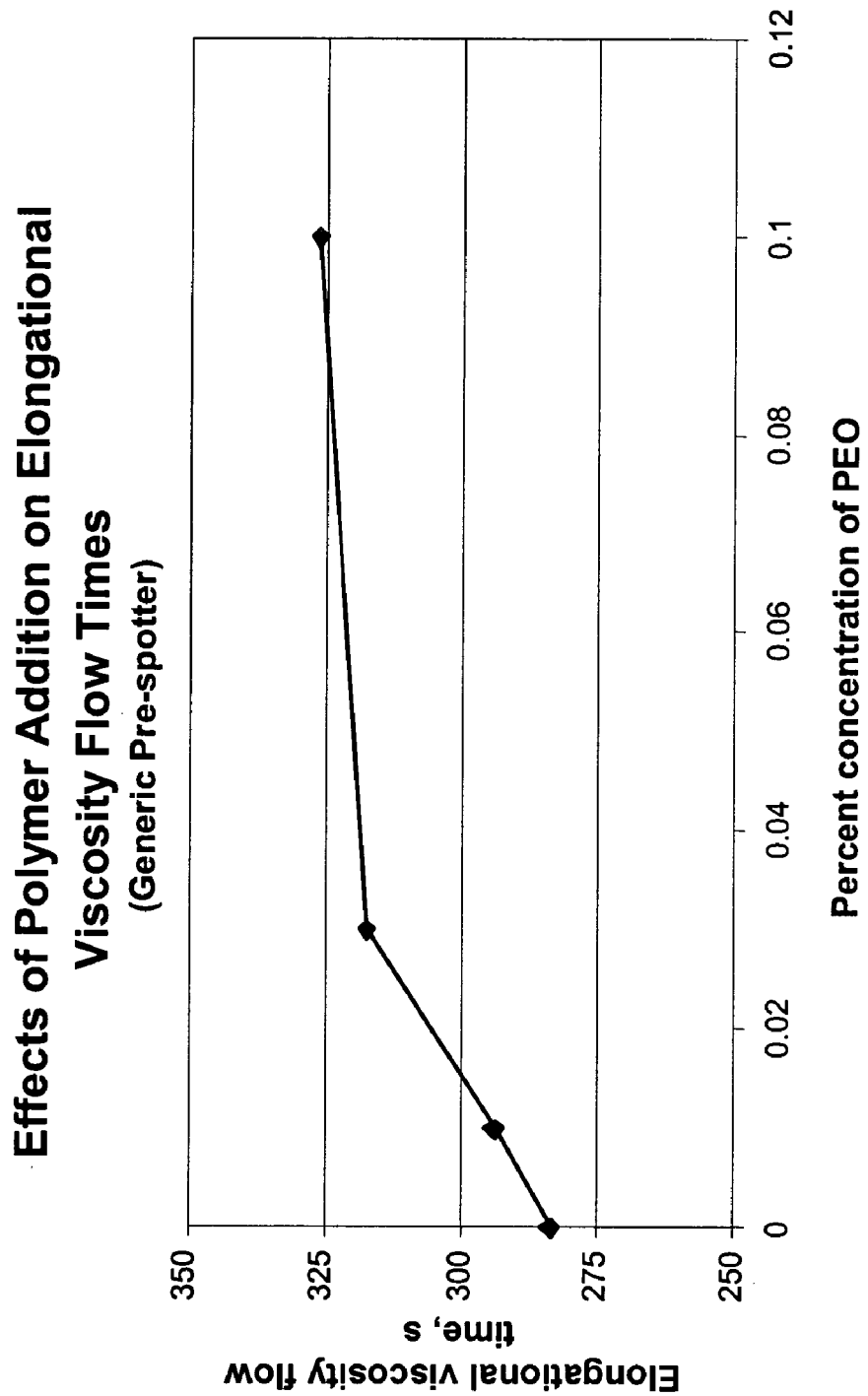
FIG. 1 is a graph showing the effects of polymer addition on elongational viscosity for a generic pre-spotter formulation.

As used herein and in the appended claims, the singular "a", "an" and "the" includes the plural reference unless the context clearly dictates otherwise. Thus, for example, reference to a "particle" includes a plurality of such particles. Unless defined otherwise, all technical and scientific terms used herein have the same meanings as commonly understood by one of ordinary skill in the art to which the invention pertains.

I. Definitions

The term "high molecular weight polymer" as used herein means a water-soluble organic molecule consisting of many repeating segments called monomers or "mers" wherein the molecular weight is at least greater than about 200,000, and preferably greater than about 400,000. The molecular weight of a high molecular weight polymer is measured by using well-known chemical and physical methods. These methods include colligative property measurement, light-scattering techniques, GPC analysis, ultra centrifugation and the like.

The term "anti-misting composition" refers to the high molecular weight polymer compositions and enzyme/high molecular weight polymer compositions according to the invention herein. The addition of the high molecular weight polymer to a composition reduces the tendency of the composition or formulated composition to generate aerosol particles. The high molecular weight polymers according to the invention are referred to herein as anti-misting agents because of their ability to reduce aerosol generation in a given environment. Anti-misting compositions as used herein include formulated or re-formulated personal care and cleaning product compositions.

The phrase "a formulated or reformulated personal care product" or "formulated with a personal care product" refers to the high molecular weight polymer composition according to the invention, either alone or in combination with an enzyme or enzyme formulation, which is further combined with components of a personal care product.

The phrase "a formulated or reformulated cleaning product" or "formulated with a cleaning product" refers to the high molecular weight polymer composition according to the invention, either alone or in combination with an enzyme or enzyme formulation which is further combined with components of a cleaning product composition.

A "corresponding composition" refers to a composition, personal care product or cleaning product that does not include the high molecular weight polymer as disclosed herein.

Aerosol particles are airborne dispersions of small particles or droplets that when dispensed into the atmosphere remain suspended or are transported by the atmosphere for a substantial period of time, at least 5 seconds, and more commonly for 30 seconds and up to 10 minutes or more after dispensing. Aerosols may be generated from solutions, suspensions, emulsions, semi-solid preparations, gels and the like. Aerosols or aerosol sprays may have a wide particle size distribution. Aerosol particles are generally considered to be 500 μm or less, and generally in the range of 0.1 μm to 100 μm. Aerosol particles may also be subdivided into a respirable range, which are particles that may enter the lungs, and an inspirable range, which are particles that pass through the nasal passage-way. Respirable particles are generally about 0.1 μm to 25 μm and inspirable particles are generally about 100 μm or less. In one embodiment of the invention the high molecular weight polymer reduces the respirable particles.

The terms "aerosol", "aerosol particles", "mist" and "mist droplets" are used interchangeably herein.

Dv is a measure of particle or droplet diameter. $Dv_{10}$ represents the particle diameter below which 10% of the aerosol spray volume is contained. $Dv_{50}$ represents the volume median diameter (vmd) such that 50% of the spray volume is contained in droplets larger than the vmd and 50% of the spray volume is contained in droplets smaller than the vmd. $Dv_{90}$ represents the particle diameter above which 10% of the spray volume is contained.

In an embodiment of the invention, the $Dv_{50}$ of the anti-misting compositions will be between about 50 μm-250 μm. In another embodiment the $Dv_{50}$ will be between about 55 μm-200 μm. In yet another embodiment the $Dv_{50}$ will be between about 65 μm-150 μm, and in a further embodiment the $Dv_{50}$ will be between about 75 μm-125 μm. In a preferred embodiment the $Dv_{50}$ is about 100 μm. One skilled in the art is aware that the aerosol particle distribution may be influenced by the dispensing means. Therefore in another embodiment, the $Dv_{50}$ of the anti-misting compositions according to the invention will be at least 10%, 20%, 30%, 40%, 50%, 60%, 70%, 80%, 90%, 100%, 125%, 150%, 200% or greater than the $Dv_{50}$ of a corresponding composition without the high molecular weight polymer when both compositions are tested under essentially the same conditions. In yet another embodiment, the $Dv_{50}$ of the compositions according to the invention will be between 10%-200%, between 10%-150%, between 20%-150% and between 40%-80% greater than the $Dv_{50}$ of a corresponding composition without the high molecular weight polymer when tested under essentially the same conditions.

The anti-misting compositions according to the invention comprising a high molecular weight polymer either with or without an enzyme may be dispensed through an orifice by various means. These dispensing means include but are not limited to spraying, pumping, atomizing, squirting, degassing, gassing, propelling, effervescing, or any means wherein sufficient shear or velocity is introduced into a liquid stream resulting in the breakup of the stream into aerosol particles. As one skilled in the art is well aware the geometry of an orifice opening or valve and the pressure used to dispense a composition can influence the particle size distribution.

"Product bounce-off" or "product re-bounding" refers to the breakup of a formulated product into airborne particles, and particularly to the breakup of particles which form aerosols upon impact with a target material. In an embodiment of the invention, a high molecular weight polymer will increase the $Dv_{50}$ of particles rebounding from a target material. In another embodiment the high molecular weight polymer reduces the quantity of particles rebounding from a target material.

"A target material" as used herein includes a hard surface, such as glass, metal, ceramic, porcelain, wood, plastics including FORMICA and CORIAN, and the like; a natural or synthetic textile surface, such as cotton, wool, silk, rayon, polyester, LYCRA, nylon, spandex, and the like; and a body surface, such as hair, skin or teeth.

The term "viscosity" means a measure of the resistance to flow of a fluid and includes two forms; shear viscosity ($\eta_s$) and elongational viscosity ($\eta_e$). Shear viscosity represents the resistance of adjacent layers in a liquid sliding over each other and elongational viscosity represents resistance of the fluid to being stretched or contracted.

The term "effective amount of an enzyme" or "effective amount of an enzyme formulation" means the amount of enzyme in a composition or formulation that is effective for its intended use. This amount will differ depending on the use of the final formulation. The amount of enzyme required to be effective in a shower gel may be different than the amount of enzyme required to be effective in a liquid dish detergent. In one embodiment, when one or more enzymes are included in a composition according to the invention, the enzyme activity is essentially not affected by the high molecular weight polymer.

All percentages and ratios recited herein are "by weight" unless otherwise specified.

II. Detailed Description of the Invention

The compositions and formulations of the invention typically comprise a high molecular weight polymer and are referred to herein as anti-misting compositions. In one embodiment the anti-misting compositions include a high molecular weight polymer combined with an enzyme in an aqueous composition. The anti-misting compositions of the invention may contain a variety of other optional ingredients as described herein below:

A. Components

High Molecular Weight Polymers

Various examples of high molecular weight polymers include a) polyethylene oxides, such as POLYOX, supplied by Dow Chemical Co. Midland, Mich.; b) polyacrylamides, such as TARGET LC, supplied by Loveland Industries, Greeley, Co., having a molecular weight between $2.5 \times 10^7$ and $4.0 \times 10^7$; c) hydroxypropyl guar gum, such as AgRHO DR2000, supplied by Rhodia, France; d) substituted acrylamides containing sulfonate groups, such as poly(2-acrylamido-2-methylpropane sulfonic acid), also known as POLYMER 2000, supplied by Clariant, Charlotte, N.C.); e) other acrylamide copolymers, such as poly(acrylamide/acrylic acid); f) other gums, for example, locust bean and guar gums; and g) mixtures thereof.

In one preferred aspect, the high molecular weight polymer is a polyethylene oxide. Polyethylene oxides (PEOs) are also known in the art as polyethylene glycols (PEGs). The PEOs useful herein have a molecular weight of from $0.4\times10^6$ to $7\times10^6$; $0.8\times10^6$ to $4\times10^6$, and $1\times10^6$ to $3.0\times10^6$. Most preferably the molecular weight is about $1.5\times10^6$ to $2.5\times10^6$. These materials are available for example, under the name POLYOX from Dow Chemical Company, Midland, Mich. One preferred POLOXY is known by the INCI name PEG-45M. The polymers can be prepared by the polymerization of ethylene oxide, utilizing an alkaline earth metal oxide as a catalyst. In one preferred aspect the level of PEO in the compositions is about $1.0\times10^{-4}$% to about 10%, about $1.0\times10^{-4}$% to about 5%, about $1.0\times10^{-4}$% to about 2%, about $1.0\times10^{-4}$% to about 1.5%, about $1.0\times10^{-3}$% to about 10%, about $1.0\times10^{-2}$% to about 10%, about $1.0\times10^{-2}$% to about 5%, about 0.1% to about 5%, about 0.1% to about 2% and about 0.5% to about 5%. In another preferred aspect, the high molecular weight polymer is a polyacrylamide. Exemplary polyacrylamides are those sold under the names TARGET LC supplied by Loveland Industries, Greeley, Co., molecular weight $2.5\times10^7$ to $4.0\times10^7$. These polymers can be prepared by the polymerization of acrylamide. The general properties of acrylamide polymers as well as their methods of preparation are disclosed in THE ENCYCLOPEDIA OF POLYMER SCIENCE AND ENGINEERING vol.1, John Wiley & Sons, (1985) pgs 169-211. In one preferred aspect the level of polyacrylamide or copolymer thereof in the compositions is about $1.0\times10^{-4}$% to about 25%; about $1.0\times10^{-4}$% to about 10%, about $1.0\times10^{-4}$% to about 5%, about $1.0\times10^{-4}$% to about 2%, about $1.0\times10^{-4}$% to about 1.5%, about $1.0\times10^{-3}$% to about 10%, about $1.0\times10^{-2}$% to about 10%, about $1.0\times10^{-2}$% to about 5%, about 0.1% to about 5%, about 0.1% to about 2% and about 0.5% to about 5%.

When an aqueous droplet is directed against a target material at a velocity (V1) there are two phases involved in the droplet break-up process. The first phase is the impaction and expansion phase. In this phase the degree of droplet break-up is directly proportional to inertial factors, such as density of the liquid ($\rho$), impact velocity of the liquid ($V_l$) and the initial droplet diameter ($D_o$) and inversely proportional to the resistance factors of surface tension ($\sigma$) and viscosity ($\eta$). The higher the surface tension ($\sigma$) and the higher the viscosity the less the tendency to form small droplets on break-up. Viscosity can take on two forms, shear viscosity ($\eta_s$) and elongationalviscosity ($\eta_e$). The provision of the flexible water-soluble polymers of the present invention is believed to enhance at least elongational viscosity The second phase in the droplet break-up process is the retraction phase where after a droplet reaches a maximum diameter (Dmax), the droplet retracts and can cause additional small droplet formation in the process. The greater the retraction velocity the greater the tendency to form very small particles called fines. The retraction velocity is inversely proportional to the elongational viscosity and directly proportional to the surface tension.

Other factors which may control the breakup of the delivered mist droplet include roughness amplitude of the surface, roughness wavelength of the surface and the advancing and receding contact angles between the liquid and the target surface. For further discussion of these properties reference is made to Rioboo, et al., (2001) *Atomization and Sprays,* 11: 155-165 and Bergeron et al., (2000) *Nature* 405:722-775.

While not meant to be limited to any particular theory, it is believed that the mechanism of action of the high molecular weight polymers as an anti-misting agent may be due to an increase in either, or both, shear viscosity or elongational viscosity.

Enzymes and Enzyme Formulations

One or more enzymes that may be incorporated into the compositions of the invention include enzymes selected from amylolytic enzymes, proteolytic enzymes, cellulytic enzymes, and oxidoreductase enzymes. Examples of these enzymes include, but are not limited to, amylases, proteases, lipases, laccases, phenol oxidases, oxidases, cellulases, esterases, peroxidases, phytases, isomerases, mannases, and pectinases. Preferably the enzyme to be included in the anti-misting compositions, which include compositions of formulated personal care products and cleaning products, are proteases, lipases, cellulases and amylases, particularly proteases.

Proteases may be naturally occurring proteases or recombinant proteases. Two types of proteases are well known and these include neutral (or metalloproteases) and alkaline (or serine proteases). Serine proteases are enzymes which catalyze the hydrolysis of peptide bonds in which there is an essential serine residue at the active site. The serine proteases have molecular weights in the 25,000 to 30,000 range (Priest (1977) *Bacteriol. Rev.* 41:711). A preferred serine protease is subtilisin. A wide variety of subtilisins have been identified and sequenced from bacterial and fungal sources. Examples of bacterial sources of subtilisin include *Bacillus* species such as. *B. subtilis, B. licheniformis, B. lentus*, and *B. amyloliquefaciens*. Well known subtilisins include but are not limited to, subtilisin 168, subtilisin BPN', subtilisin 147, subtilisin 309, subtilisin PB92, and subtilisin Carlsberg. For a review of subtilisin like serine proteases reference is made to Siezen et al. (1991) *Protein Engineering* 4:719 and to the more recent reviews of Siezen et al. (1997) *Protein Sci.* 6:501 and P. N. Bryan (2000) *Biochim. Et. Biophy. Acta.* 1543:203.

One of general skill in the art is aware that the amino acid sequences of the subtilisin members are not entirely homologous, but this class of serine proteases shares a common amino acid sequence defining a catalytic triad which distinguishes them from other related classes of serine proteases. The relative order of these amino acids, reading from the amino to carboxy terminus, is aspartate-histidine-serine. Thus, subtilisin herein refers to a serine protease having the catalytic triad of subtilisin related proteases.

"Recombinant," "recombinant subtilisin" or "recombinant protease" refers to an enzyme, subtilisin or protease in which the DNA sequence encoding the enzyme, subtilisin or protease is modified to produce a variant (or mutant) DNA sequence which encodes the substitution, deletion or insertion of one or more amino acids in the naturally-occurring amino acid sequence. Reference is made to the following publications which teach variant proteases: U.S. Pat. No. 4,760,025 (U.S. RE 34,606); U.S. Pat. No. 5,185,258; 5,204,015 ; 5,441,882; 5,631,217 5,665,587; 5,700,676; 5,741,694; 5,880,080; 6,197,567; 6,218,165; WO 89/06279; WO 92/10755; WO 99/49056 and WO 01/07579. In a preferred embodiment, the subtilisin of the compositions are native-type or recombinant subtilisins which have been further modified.

Proteases are used in many products, and commercially available proteases include those sold under the trade names MAXACAL, MAXAPEM, MULTIFECT, PROPERASE, PURAFECT, OPTICLEAN, and OPTIMASE (Genencor International, Inc., Palo Alto, Calif.) and ALCALASE, SAVINASE, PRIMASE, DURAZYM, ESPERASE (Novozymes A/S Denmark).

Commercially available amylase enzymes include those sold under the trade names MAXAMYL and PURAFECT (Genencor International, Inc., Palo Alto, Calif.) and TER- MAMYL and BAN (Novozymes A/S Denmark). Amylase enzymes are also disclosed in WO 96/23873.

Commercially available lipases include those sold under the trade names LIPOMAX and LUMAFECT (Genencor International, Inc.) and LIPOLASE (Novozymes A/S, Denmark). Lipase enzymes are also described in EP-B-0218272.

Commercially available cellulases include those sold under the trade names CAREZYME and CELLUZYME (Novozymes A/S, Denmark) and PURADAX and Detergent cellulase L (Genencor International, Inc.).

In one embodiment the anti-misting compositions include compositions comprising one or more enzymes combined with the high molecular weight polymer. In this embodiment the amount of enzyme comprising the composition may be between about $1.0 \times 10^{-4}\%$ to about 25%; between about $1.0 \times 10^{-3}\%$ to about 20%; between about $1.0 \times 10^{-3}\%$ to about 15%; between about $1.0 \times 10^{-3}\%$ to about 10%; and between about $1.0 \times 10^{-3}\%$ to about 5% enzyme. The amount of high molecular weight polymer comprising the anti-misting composition is about $1.0 \times 10^{-4}\%$ to about 25%; about $1.0 \times 10^{-4}\%$ to about 10%; about $1.0 \times 10^{-4}\%$ to about 5% or about $1.0 \times 10^{-4}\%$ to about 1% whether or not an enzyme is included in the composition. When one or more enzymes are included the ratio of enzyme to polymer in the compositions may be about 1:250 to about 250:1; about 1:100 to about 100:1; about 1:50 to about 50:1; about 1:25 to about 25:1; about 1:10 to about 10:1; about 1:5 to about 5:1; about 1:1 to about 4:1; and about 1:1 to about 2:1.

Other Ingredients

The anti-misting compositions including one or more enzymes and/or the high molecular weight polymer may further include other adjunct ingredients. These ingredients include but are not limited to a) stabilizers for example, to prevent degradation of the polymer to lower molecular weight species; b) alkali metal salts such as calcium, potassium and sodium salts; c) enzyme protecting agents, cofactors or inhibitors, such as propylene glycol, glycerol, sorbitol, sucrose, trehalose, sodium formate, sodium acetate, sodium borate, betaine, ammonium sulfate, ammonium citrate, urea, guanidine hydrochloride, guanidine carbonate, guanidine sulfamate, thiourea dioxide, monoethanolamine, diethanolamine, triethanolamine, amino acids such as glycine, sodium glutamate and the like, phenylboronic acid and phenyl boronate derivatives, peptide inhibitors and the like, calcium salts such as calcium chloride, calcium formate and the like; d) scavengers of chlorine, hypochlorite, hydrogen peroxide and other pro-oxidants which can be detrimental to enzymes, e.g. ammonium sulfate, amino acids, ascorbic acid, sodium citrate, salts of iron and other heavy metals and the like; and e) other minor ingredients such as proteins e.g. bovine serum albumin, casein and the like; surfactants including anionic surfactants, ampholytic surfactants, nonionic surfactants, cationic surfactants and long-chain fatty acid salts; metallic salts for example to avoid excessive gelling of the polymer in a dispensing device; builders; alkalis or inorganic electrolytes; caking inhibitors and solubilizers such as nonionic surfactants and hydrotropes; activators; antioxidants; dyes; bleaching agents; bluing agents whiteners; inhibitors; binders; and fragrances. One skilled in the art is referred to McCutcheon's, DETERGENTS AND EMULSIFIERS, Vol 1. and FUNCTIONAL MATERIALS, Vol. 2 International and North American Editions (1999), MC Publishing Co.; U.S. Pat. No. 4,421,769 and WO 00/24372.

Table 1 lists non-limiting examples of anti-misting compositions according to the invention.

TABLE 1

| Raw material | Amount % | Amount % | Amount % | Amount % | Amount % |
|---|---|---|---|---|---|
| Protease | 0 | 0 | 4.0 | 2.0 | 0 |
| Amylase | 0 | 0 | 0 | 0 | 4.0 |
| PEO | 2.5 | 0 | 1.0 | 0 | 0.8 |
| TARGET LC | 0 | 5.0 | 0 | 1.0 | 0 |
| Propylene glycol | 10.0 | 20 | 50.0 | 65.0 | 0 |
| Sucrose | 0 | 0 | 0 | 0 | 30.0 |
| Sodium Formate | 0 | 0 | 0.5 | 0.4 | 0 |
| Calcium Chloride | 0 | 0 | 0.02 | 0.02 | 0.01 |
| Deionised water | QS | QS | QS | QS | QS |

QS means quantity sufficient to bring the amount up to 100%

These concentrate compositions containing the enzymes and/or high molecular weight polymer may be further formulated into formulated personal care products or formulated cleaning products as discussed herein below.

B. Methods of Making the Invention

Preparation of anti-misting compositions according to the invention may be accomplished with apparatus and techniques known in the art. Various general embodiments are disclosed below.

In a first embodiment, a high molecular weight polymer is mixed with various water miscible organic solvents, such as propylene glycol or glycerol until the polymer is fully dispersed. Water is added to the mixture followed by other solid ingredients such as calcium chloride, sodium formate, sodium borate or other enzyme stabilizers. An enzyme, or enzyme formulation, is then added to the mixture, followed by other excipients if desired. All ingredients are mixed until homogenous. One skilled in the art is well aware that a similar composition may be prepared which lacks an enzyme.

In a second embodiment, the high molecular weight polymer according to the invention is first prepared as an aqueous solution (i.e. 2-5%) which can then be added to a mixture of water miscible organic solvents, such as propylene glycol or glycerol and other solid ingredients as mentioned above. If an enzyme is included, it is added at this point and mixed until homogeneous.

In a third embodiment, water miscible organic solvent such as, propylene glycol or glycerol is first combined with water until homogeneous, and then mixed with other solid ingredients as mentioned above. Enzyme is added followed by the high molecular weight polymer and all ingredients are mixed until homogenous.

In a fourth embodiment, if an enzyme is combined with the high molecular weight polymer, the enzyme may be added directly to the polymer mixture or an enzyme composition can be prepared first and then the polymer mixture is added to the enzyme composition.

In a fifth embodiment, the high molecular weight polymer is first prepared as an aqueous solution (e.g., 2-5%) and then added to an aqueous polyol solution (e.g. 5-50% sucrose, sorbitol, trehalose or other sugar). Other ingredients, such as calcium chloride are added and followed by addition of an enzyme such as amylase. The composition is mixed until homogenous.

Those skilled in the art will recognize that preparation of the anti-misting formulations of the present invention may be performed using procedures which include conditions selected to maintain the molecular weight of the selected polymer. Such conditions include, for example, mixing methods, mixing times and temperatures that do not unduly disrupt the bonds of the selected polymer. Suitable preparation methods for polyethylene oxides include, but are not limited to, manufacturing instructions provided by Dow Chemical Co. (Midland, Mich.) for POLYOX, and the earlier cited methods in The Encyclopedia of Polymer Science and Engineering vol. 1 (previously cited).

Preferably once the compositions, as generally described above are prepared, they are further incorporated into a personal care or cleaning product to form formulated compositions thereof. It is further emphasized that the high molecular weight polymer compositions according to the invention may be formulated with a personal care or cleaning product wherein the high molecular weight polymer composition does not include an enzyme. Further an enzyme composition may be combined directly with a high molecular weight polymer composition and then incorporated into the personal care or cleaning product. Additionally an enzyme composition may be stored separately from the high molecular weight polymer composition and separately be incorporated into the personal care or cleaning product.

C. Methods of Using the Invention

The high molecular weight polymer compositions as disclosed above impart desirable anti-misting properties that reduce protein exposure during manufacturing of the compositions, and the composition impart desirable anti-misting properties to further compositions or formulations when added to said compositions or formulations.

Resulting compositions will include other ingredients known in the art for the particular type of formulation and said ingredients are provided in amounts that will yield a desirable effect. The resulting compositions may comprise one or more enzymes which have been included in the composition prior to formulation with the high molecular weight polymer.

The resulting anti-misting compositions according to the present invention may be packaged in pump spray devices, pressured aerosol sprays and various containers well known in the art.

The resulting anti-misting compositions of the invention are commonly dispensed onto a target material using a pump spray. In general, when the orifice or spray head valve is open pressure forces the aqueous contents through the orifice. Both the pressure of the dispensing means and the orifice valve geometry will influence the aerosol spray pattern and particle size distribution.

While pumping and spraying are primary mechanisms contributing to the formation of aerosols, the anti-misting compositions of the invention may be applied by pouring, by hand application or may be further incorporated onto a fiber cloth, wash cloth, wipe or other solid dispensing substrate designed for direct rubbing or contact on to the target material. In such applications, the generation of aerosols may occur by subsequent processes such as rinsing, spraying showering or other direct impingement of water or aqueous solutions upon a target material already coated or covered with the anti-misting composition.

The resulting anti-misting compositions of the invention generally fall into two groups; formulated personal care products and formulated cleaning products.

(1) Personal Care Formulations

The aqueous high molecular weight polymer compositions according to the invention incorporated into a personal care formulation imparts aerosol control.

Personal care products include but are not limited to shower and bath gels; shaving creams or gels; hair products such as shampoos, conditioning shampoos, cream rinses and hairsprays; bar soaps; liquid hand soaps; body or face lotions and creams; facial masques; toothpaste; and mouthwash. In particular when these products are used in a shower environment there is a potential for aerosolization, particularly product bounce-off.

Typically, the personal care formulation will be prepared according to the customary protocol for the product. For example, if the anti-misting compositions are included in a shower gel, the shower gel may be formulated first and then the anti-misting composition is added to the shower gel formulation. However, the anti-misting composition may also be formulated concurrently with the ingredients comprising the shower gel to form the finished product. Upon completion of the formulation of the finished product, the formulation will be packaged in a suitable form.

When the anti-misting compositions are formulated with a personal care product, the formulations may include a final concentration of about 0.0001% to about 10% high molecular weight polymer. Preferably about 0.0001% to about 5.0% high molecular weight polymer, about 0.001% to about 1.0%, about 0.001% to about 0.5%; and about 0.01% to about 0.1% high molecular weight polymer. When the anti-misting compositions include both enzyme and high molecular weight polymer, the formulations include about 0.0001% to about 20% enzyme; about 0.0001% to about 10% enzyme; about 0.001% to about 10% enzyme; about 0.01% to about 10% enzyme; about 0.01% to about 5.0% enzyme; about 0.1% to about 10%; about 0.1% to about 5% enzyme; or about 0.5% to about 5% enzyme.

Additionally, in one embodiment, the $Dv_{50}$ of the formulated compositions will be between 10-200% greater than the $Dv_{50}$ of the corresponding formulation without the high molecular weight polymer.

The volume of product mist from direct spray, plus/minus rebound, will be decreased from about 5 to 95%; about 10 to 90%, about 10 to 80%, or about 10 to 50%. The volume of product mist from direct spray, plus/minus rebound, can be easily measured when an enzyme is combined with the cleaning product formulation by measuring the amount of enzyme collected by an air sample before and after the high molecular weight polymer composition is added to the personal care product.

A comprehensive list of ingredients that may be included in personal care products is found in the International Cosmetic Ingredient Dictionary and Handbook, 9th Ed. (2002) Cosmetic, Toiletry and Fragrance Association. Reference is also made to U.S. Pat. No. 5,863,597. Non-limiting examples of personal care formulations including the anti-misting compositions according to the invention include:

TABLE 2

MOISTURIZING SHOWER GEL pH = 7

| RAW MATERIAL | Amount (%) |
|---|---|
| Deionised Water | QS |
| Glycerin | 4.0 |
| PEG-6 Caprylic/Capric Glycerides | 4.0 |
| Palm Kernal Fatty acids | 3.0 |
| Sodium Laureth-3 Sulphate | 45.0 |
| Cocamide MEA | 3.0 |
| Sodium Lauroamphoacetate | 25.0 |
| Soyabean Oil | 10.0 |
| Polyquaternium-10 (JR30M) | 0.70 |
| Protease/PEO | 1.0 |

In this example a shower gel formulation is combined with a protease/PEO composition in a 10:1 ratio. "Minors" are inclusive of:pH modifiers, preservatives, viscosity modifiers, dyes, and perfumes. Amounts represent approximate weight percent, unless otherwise indicated, and are not intended to indicate significant digits.

TABLE 3

BODY WASH

| RAW MATERIAL | pH 6.5 Amount | pH 7.0 Amount | | pH 8.5 Amount |
|---|---|---|---|---|
| Deionised Water | QS | QS | QS | QS |
| Sodium Laureth Sulphate | 12 | 15 | 15 | 8 |
| Cocamidopropyl Betaine | 8 | 10 | 10 | 15 |
| APG Glucoside (Plantacare 2000) | 0 | 2 | 2 | 1 |
| Polyquaternium-10 (JR30M) | 0.25 | 0 | 0 | 0 |
| Protease | 0.5 | 1.0 | 1.0 | 0.5 |
| PEO | 0.1 | 0.5 | 1.0 | 0.5 |
| Polyquaternium-7 (Mackam 55) | 0 | 0 | 0 | 0.7 |

In this example a bodywash formulation is combined with PEO or PEO/protease composition.

(2)—Cleaning Formulations

The aqueous high molecular weight polymer compositions according to the invention added to a cleaning product formulation impart aerosol control. Cleaning formulations include but are not limited to detergent formulations, such as liquid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters.

When these products are used in a desired environment there is a potential for both aerosol generation by dispensing the product onto a target material and by product bounce off. For example, when a glass cleaning formulation is used on a countertop, one may be exposed to aerosol generation from spraying the formulation on to the counter top and one may also be exposed to aerosol generation from the formulation bouncing off the counter top. In another example when a pre-spotter is used on a target material such as cotton cloth, one may be exposed to aerosol generation from the formulation by bouncing off the cloth. The invention as described herein reduces the aerosol generation from these formulated products.

As described above typically, the cleaning formulation will be prepared according to the customary protocol for the product. For example, if the anti-misting compositions are included in a pre-spotter cleaning product, the pre-spotter may be formulated first and then the anti-misting composition is added to the pre-spotter formulation. If the cleaning formulation must be heated to aid in the solubility of any ingredients, the anti-misting composition will be added after the pre-spotter formulation is completed. However, the anti-misting composition may also be formulated concurrently with the ingredients comprising the pre-spotter to form the finished product. Upon completion of the formulation the finished product will be packaged in a suitable form.

When the anti-misting compositions are formulated with a cleaning care product, the formulations may include a final concentration of about 0.0001% to 10% high molecular weight polymer. Also about 0.0001% to about 5.0%; about 0.001% to about 1.0%; about 0.001% to about 0.5%; and about 0.01% to about 0.1%. When the anti-misting compositions include both an enzyme and a high molecular weight polymer the formulations may include about 0.001% to about 10% enzyme. Also about 0.001% to about 5.0%; about 0.01% to about 10% enzyme; about 0.01% to about 5.0%; about 0.1% to about 5% enzyme; about 0.1% to about 1.0%; or about 0.5% to about 5% enzyme.

Additionally, in one embodiment the $Dv_{50}$ of the formulated compositions will be between about 10-200% greater than the $Dv_{50}$ of the corresponding formulation without the high molecular weight polymer.

The volume of product mist from direct spray, plus/minus bounce-off, of a target material will be decreased from about 5 to 95%; about 10 to 90%; about 10 to 80% or 10 to 50%. The volume of product mist from direct spray, plus/minus bounce-off, can be easily measured when an enzyme is combined with the cleaning product formulation by measuring the amount of enzyme collected by air sample before and after the high molecular weight polymer composition is added to the cleaning formulation.

Non-limiting examples of cleaning formulations including the anti-misting compositions according to the invention include:

TABLE 4

HARD SURFACE CLEANER FORMULATIONS

| Raw Materials | Formulation (A) Amount (%) | Formulation (B) Amount (%) | Formulation (C) Amount (%) | Formulation (D) Amount (%) | Formulation (E) Amount (%) |
|---|---|---|---|---|---|
| Deionised water | 89.0 | 39.0 | 39.0 | 62.0 | 62.0 |
| Sodium octane sulfonate | 3.0 | 0 | 0 | 0 | 0 |
| d-Limonene | 0.0 | 30.0 | 30.0 | 0 | 0 |
| EDTA | 1.2 | 1.0 | 1.0 | 5.0 | 5.0 |
| (Di) Ethylene glycol monobutyl ether | 3.0 | 10.0 | 10.0 | 6.0 | 6.0 |
| Fatty alkanolamide | 2.0 | 20.0 | 20.0 | 10 | 10 |
| PEO | 0 | 0.0075 | 0 | 0 | 0.008 |
| Amylase | 0 | 0 | 0 | 0.01 | 0.01 |
| PEO/protease | 0.015 | 0 | 0.01 | 0.015 | 0 |
| Sodium xylene sulfonate | 0 | 0 | 0 | 15.0 | 15.0 |

TABLE 5

LAUNDRY PRE-SPOTTER FORMULATIONS

| Raw Materials | Formulation* (A) - Amount % | Formulation (B) - Amount % |
|---|---|---|
| Deionised Water | 78.18 | 78.15 |
| Borax, 5 mole | 0.50 | 0.50 |
| Sodium Citrate | 1.00 | 1.00 |
| $CaCl_2 \cdot H_2O$ | 0.02 | 0.02 |
| Linear Alcohol Ethoxylate (Surfonic L24-4) | 10.0 | 10.0 |
| Propylene glycol | 10.0 | 10.0 |
| Protease | 0.3 | 0.3 |
| Polyox WSR-60N | 0 | 0.03 |

*formulation without enzyme, obtained from "Characterization of Aerosols Generated from a Consumer Spray Product-Phase II", The Soap and Detergent Association, Battelle Study No. N003043B, Battelle, Richland, Washington. (February 2000)

All publications and patents referenced herein are hereby incorporated by reference in their entirety. The following is presented by way of example and is not to be construed as a limitation to the scope of the claims.

Experimental

EXAMPLE 1

Candidate polymers were mixed into water and then serially diluted to concentrations in the 0.001 to 0.1% (wt/wt) level. Solutions of distilled water and the candidate polymer were exposed to significant liquid shear stress and aerosol generation was determined through droplet size spectral analysis using the Malvern Spratec laser diffraction system with RTSizer software. (Malvern Instruments Limited, UK). This system is capable of detecting droplets with diameters from 0.5 to 1000 µm. The shear stress challenge to the liquid solutions was created by forcing the liquid through a Bete PJ6 fog nozzle with an orifice diameter of 0.15 mm. The test liquid was supplied to the nozzle using compressed gas (80 pounds/in²) to prevent any pump shear degradation of the polymer. Spray clouds from the test nozzle were generated in a low-speed wind tunnel powered by a 3.5 kW electric motor with variable speed control. The air speed used was 4.2 m/s.

The reported results in Table 6 are for droplet size spectra and are averages for the collected data set.

TABLE 6

Volume mean diameters (µm) for various concentrations of polymers in distilled water

| Material | $Dv_{10}$ | $Dv_{50}$ | $Dv_{90}$ | % T |
|---|---|---|---|---|
| AgRho DP 2000 - 0.01% | 33.4 | 67.9 | 122.7 | 98.8 |
| AgRho DP 2000 - 0.003% | 22.6 | 46.2 | 94.4 | 97.7 |
| Polymer 2000 - 0.1% | 29.7 | 58.1 | 109.2 | 98.2 |
| Polymer 2000 - 0.01% | 22.0 | 46.1 | 108.0 | 97.1 |
| Polyox - 0.01% | 42.3 | 80.4 | 133.3 | 99.2 |
| Polyox - 0.003% | 28.5 | 58.1 | 108.5 | 98.4 |
| Polyox - 0.001% | 23.6 | 47.9 | 97.5 | 98.3 |
| Target LC polymer - 0.005% | 44.9 | 83.9 | 137.8 | 99.2 |
| Target LC polymer - 0.001% | 23.8 | 46.7 | 86.8 | 97.3 |
| Water (8 rep combined | 23.5 | 48.5 | 96.3 | 97.5 |

$Dv_{10}$, $Dv_{50}$ and $Dv_{90}$ are defined herein above. % T is the relative transmission through the laser. Higher transmission values (% T) indicate less spray is obscuring the beam, which indicates a reduced total volume of aerosols. For example, an increase in % T from 98% to 99% represents a significant decrease in the volume of aerosols obscuring the beam. The solutions containing anti-misting polymers had high transmission values and this is consistent with the hypothesis that the polymers will reduce the generation of mobile respirable droplets. Additionally the addition of anti-misting polymers to the spray solutions increased the overall size of the droplets within the spray cloud.

EXAMPLE 2

Shower Gels Including Polyox and Target LC Polymers

Formulations of shower gel (Zest and Olay, Procter and Gamble, Cincinnati, Ohio) and POLYOX and Target LC were prepared at varying concentrations. Tests were run as described above in example 1 using the Malvern Spraytec laser diffraction system with RTSizer software, Bete PJ6 fog nozzle and 500 kPa (80 psi) pressure. Initial tests were done on shower gels without the polymer to establish baseline behavior of the diluted product. The results showed that a lowering of the surface tension due to the presence of surfactants in the shower gel did not manifest itself as smaller particle sizes. Table 7 shows the effectiveness of reducing aerosol generation by the addition of high molecular weight polymers. These data indicate that polymer addition to shower gels increase droplet size of the solution compared to corresponding shower gels alone.

TABLE 7

Volume distribution sizes for gel solutions with polymers diluted in distilled water

| Polymer/Gel | $Dv_{10}$ | $Dv_{50}$ | $Dv_{90}$ | % Transmission |
|---|---|---|---|---|
| Zest 1% + Polyox 0.01% | 40.1 | 82.0 | 138.0 | 98.2 |
| Zest 0.1% + Polyox 0.01% | 39.3 | 83.9 | 146.8 | 99.0 |
| Zest 0.1% + Polyox 0.001% | 27.5 | 52.1 | 87.8 | 99.8 |
| Zest 1% + Target LC 0.005% | 40.3 | 77.4 | 133.5 | 98.8 |
| Zest 0.1% + Target LC 0.0005% | 39.7 | 77.0 | 132.5 | 98.9 |
| Zest 0.1% + Target LC 0.0005% | 25.2 | 49.0 | 82.4 | 99.4 |
| Olay 1% + Polyox 0.01% | 36.9 | 84.7 | 149.6 | 98.5 |
| Olay 0.1% + Polyox 0.01% | 38.7 | 82.8 | 144.2 | 98.8 |
| Olay 0.1% + Polyox 0.001% | 23.8 | 46.3 | 82.6 | 99.1 |
| Olay 1% + Target LC 0.005% | 32.1 | 68.6 | 115.1 | 98.6 |
| Olay 0.1% + Target LC 0.005% | 31.6 | 67.8 | 114.9 | 98.6 |
| Olay 0.1% + Target LC 0.0005% | 26.3 | 47.2 | 75.2 | 99.7 |
| Zest 1.0% | 23.2 | 47.5 | 91.8 | 97.4 |
| Zest 0.1% | 26.3 | 55.6 | 105.8 | 98.1 |
| Olay 1.0% | 28.1 | 55.9 | 106.6 | 97.9 |
| Olay 0.1% | 26.6 | 52.0 | 102.1 | 97.0 |
| Deionised water | 23.5 | 48.8 | 95.5 | 97.56 |

Each value is the average of 4-6 replicates in each formulation.

For the samples, Zest or Olay at 1%+Polyox at 0.01% (Table 8) the shear viscosity increased about 10% over distilled water. However, no decrease in flow rate through the nozzle or increase in rotameter reading was observed even though there was a substantial increase in $Dv_{50}$. While not meant to limit the invention in any manner, it is believed that the increase in $Dv_{50}$ is due to an increase in elongational viscosity.

For the samples, Zest or Olay at 1%+Target LC at 0.01% (Table 8) the shear viscosity increased 30-70% compared to distilled water. In this case the nozzle flow rate was substantially reduced and the rotameter reading increased both indicating increased drag along with a substantial increase in $Dv_{50}$. While not meant to limit the invention in any manner, it is believed that the increase in $Dv_{50}$ is due to an increase in shear viscosity.

The results indicate that both shear viscosity and elongational viscosity play a role in reducing aerosols.

TABLE 8

Surface Tension and Shear Viscosity of Selected Formulations Diluted in Distilled Water

| Material | σ N/m (× $10^{-3}$) | η Pa · s (× $10^{-3}$) | Flow rate[1] ml/s | Rotameter Reading[2] | $Dv_{50}$ μm |
|---|---|---|---|---|---|
| Distilled water | 72.6 | 0.986 | 0.58 | 38 | 48.8 |
| Zest 1% | 29.3 | 1.027 | | | 47.5 |
| Olay 1% | 32.3 | 1.007 | | | 55.9 |
| Polyox 0.01% | 56.8 | 1.091 | 0.57 | 38 | 80.4 |
| Target LC 0.005% | 43.0 | 1.654 | 0.46 | 55 | 83.9 |
| Zest 1% + Polyox 0.01% | 27.9 | 1.110 | 0.57 | 38 | 82.0 |
| Zest 1% + Target LC 0.005% | 33.6 | 1.457 | 0.45 | 41 | 77.4 |
| Olay 1% + Polyox 0.01% | 30.6 | 1.101 | 0.57 | 39 | 84.7 |
| Olay 1% + Target LC 0.005% | 32.5 | 1.332 | 0.46 | 40 | 68.6 |

Density is assumed constant at 20° C. (0.99823 g/ml) for all fluids.
[1] Actual measurement of volume flow per unit time.
[2] Placed in series (upstream) with nozzle.

EXAMPLE 3A

Laundry Spray Pre-Spotter Anti-Misting Enzyme Compositions

This example characterizes the range of airborne enzyme concentrations of a spray pre-spotter of the composition shown in Table 5. A spray pre-spotter is used to pre-treat articles of clothing prior to washing. The spray pre-spotter formulation included enzyme, a protease supplied as Purafect 4000L, either with or without the polymer Polyox. The pre-spotter was sprayed on white 100% cotton men's undershirts which were washed prior to the study with non-enzyme containing detergent to remove any sizing material. Spray formulations included 0.3% enzyme with or without 0.03% Polyox.

Sampling took place in a 20-25 cubic meter test room with no mechanical ventilation during the experiment. However an 8 minute purge cycle was conducted between samples to minimize a cumulative effect of remaining aerosols on the following samples. Temperature was controlled in the room to between 65-68° F.

Sampling was conducted using a Graysby HV2000P, high flow sampling pump (Graysby). Enzyme aerosols were collected on a 11 cm² glass fiber filter and the pump was calibrated at 440 liters per minute.

Formulations were sprayed under normal conditions, which are defined as the treatment of 3 test articles with 5 sprays per test article using manual actuation of the spray mechanism. The sprays were delivered at 1 per second for 5 seconds, followed by a 10 second interval between target articles. The total spraying time is about 40 seconds. A two-minute sample was collected for each replicated formulation.

The test articles were place flat on a horizontal surface and sprayed. The sample was collected at 20 inches from the test article. The sprayer, equipped with a nozzle from a commercially available laundry pre spotter, was oriented at a 45 degree angle from the test article and at least 5 inches from the target. An enzyme:substrate interaction assay utilizing spectrophotometry was used to analyze the samples. Time weighted average (TWA) airborne enzyme concentrations in nanograms per cubic meter of air (ng/M³) were determined and the results are presented in Table 9A. With a 71% enzyme recovery rate, Polyox reduced the concentration of enzyme by approximately 53% when the values are averaged.

TABLE 9A

Spray Test for Laundry Prespotter Containing 0.3% Enzyme

| Sample No. | Formulation % enzyme | Minus Polyox TWA (ng/M³) | With Polyox (0.01%) TWA (ng/M³) |
|---|---|---|---|
| 1 | 0.3% | 638. | 162. |
| 2 | 0.3% | 592. | 162. |
| 3 | 0.3% | 558. | 164. |
| 4 | 0.3% | 268. | 164. |
| 5 | 0.3% | 372. | 458. |
| 6 | 0.3% | 453. | 318. |
| 7 | 0.3% | 697. | |
| Average Value | | 511. | 238. |

EXAMPLE 3B

Laundry Spray Pre-Spotter Anti-Misting Enzyme Compositions

A Second experiment testing polymer addition to enzyme pre-spotter formulations was conducted using a protocol obtained from "Characterization of Aerosols Generated from a Consumer Spray Product-Phase II", The Soap and Detergent Association, Battelle Study No. N003043B, Battelle, Richland, Wash. (February 2000). The test protocol included automated spray trigger actuation using a solenoid. The spray bottle was equipped with a Saint-Gibain Calmar TS-800-1 spray nozzle and was oriented in a vertical position in relation to the test garment. The nozzle was placed 6 inches from the test garment and 10.25 inches from the table surface. The experiments were conducted in a 7.57 M³ test chamber with no mechanical ventilation. Ambient temperature in the chamber was between 20-27° C. and test formulations were maintained at a temperature of 20-23° C.

The polymer was prepared by dissolving 2.0 grams of PEO powder (POLYOX)WSR N60K) in 8.0 grams of a water miscible nonsolvent (propylene glycol or saturated sodium chloride) prior to addition to the enzyme concentrate. To prepare a 200 gram batch, the PEO powder and the nonsolvent were place in a 400 ml beaker equipped with a propeller located at the 50 ml. level of the beaker. The diameter of the beaker and the diameter of the propeller were 2.75 and 2.50 inches, respectively. Operation of the propeller pushed the fluid towards the bottom of the beaker. The polymer batch was added to 190 grams of Purafect 400L enzyme concentrate. The mixing rate was about 60 rpm, the mixing time was between about 4 hours, and the temperature was about 35° C.

White 100% cotton T-shirts, previously laundered with non-enzyme containing detergent to remove sizing material and other residue, were treated with 5 sprays of each pre-spotter with a 1 second interval between sprays. A Graysby HV2000P high flow sampling pump (Graysby) calibrated at 410 liters per minute was used to collect enzyme aerosols on a 11 $cm^2$ glass fiber filter. An enzyme:substrate interaction assay utilizing spectrophotometry was used to analyze the samples. Replicate samples of each formulation tested were collected including a background sample before and after each set of replicates.

Table 9B shows the results for a first set of samples comparing the generic pre-spotter formulation of Table 5 with varying amounts of enzyme and polymer. Specifically, the enzyme content of the pre-spotter was 1% and 0.5% Purafect 4000L, and the polymer was 0.01% and 0.005% Polyox. Enzyme concentration was reduced by about 95% when 0.005% PEO was added to pre-spotter, and the reduction was about 99% when 0.01% PEO was added to pre-spotter.

Table 9C shows the results for a second set of samples using 5 generic pre-spotter formulations, all including 0.5% Purafect 4000L and 0%, 0.0025%, 0.0050%, 0.0100% and 0.0150% Polyox. The results demonstrate about 27%, 84%, 91% and greater than 95% reduction in enzyme concentrations for formulations containing, respectively, 0.0025%, 0.0050%, 0.0100% and 0.0150% Polyox.

TABLE 9B

Spray Test for Laundry Prespotter Containing 0.5 and 1% Enzyme and Varying PEO Concentrations (enzyme concentration in collected air expressed in $ng/m^3$)

| Replicate Samples | 1% Enzyme 0% PEO | 1% Enzyme 0.01% PEO | 0.5% Enzyme 0% PEO | 0.5% Enzyme 0.005% PEO |
|---|---|---|---|---|
| 1 | 1638. | 46. | 379. | 43. |
| 2 | 2120. | 49. | 426. | <23. |
| 3 | 2203. | <23. | 499. | <23. |
| 4 | 1777. | <23. | 517. | <23. |
| 5 | 2031. | 24. | 707. | <23. |
| 6 | 1986. | 46. | 574. | <23. |
| 7 | 2058. | 26. | 599. | <23. |
| Average | 1973. | 32. | 529. | <23. |

TABLE 9C

Spray Test for Laundry Prespotter Containing 0.5% Enzyme and Varying Concentrations of PEO (enzyme concentration in collected air expressed in $ng/m^3$)

| Replicate Samples | 0.5% Enzyme 0% PEO | 0.5% Enzyme 0.0025% PEO | 0.5% Enzyme 0.0050% PEO | 0.5% Enzyme 0.0100% PEO | 0.5% Enzyme 0.0150% PEO |
|---|---|---|---|---|---|
| 1 | 379. | 582. | 133. | 73. | 30. |
| 2 | 426. | 241. | 104. | 50. | 50. |
| 3 | 499. | 382. | 125. | 28. | <23. |
| 4 | 517. | 367. | 49. | 41. | <23. |
| 5 | 707. | 417. | 65. | 42. | <23. |
| 6 | 574. | 361. | 44. | 47. | 27. |
| 7 | 599. | 349. | 66. | 51. | <23. |
| Average | 529. | 386. | 84. | 48. | <28. |

EXAMPLE 4

Volume Distribution Sizes for a Detergent with and without Polymer

An air-atomization nozzle was used to spray samples of a commercially available liquid laundry detergent (Purex), with and without added polymer, through the Malvern Spratec laser diffraction system described in Example 1. The dual port nozzle Spraying Systems Co., Wheaton, Ill., ¼ JBC nozzle, #60100 fluid cap, and #1401110 air cap) supplied liquid at 30 psi through one port and compressed air at 60 psi through the second, adjacent port. Spray clouds from the test nozzle were generated in a wind tunnel powered by a 3.5 kW electric motor with variable speed control. The air speed was set at 7 m/s.

The addition of 0.5% anti-misting polymer (PEO) to the liquid detergent increased the overall size of the droplets within the spray cloud, as shown in Table 10 below.

TABLE 10

Detergent Spray Test Using Dual Port Nozzle Volume mean diameters (m) liquid detergent with/without polymer

| Material | $Dv_{10}$ | $Dv_{50}$ |
|---|---|---|
| Purex - 0% PEO | 6.1 | 70.5 |
| Purex - 0.05% PEO | 9.3 | 853 |

EXAMPLE 5

Laundry Pre-Spotters with and without Polymer

The generic laundry pre-spotter formulation in Table 5 without the enzyme and with 78.48% water instead of 78.18% water (G), and four commercially available laundry pre-spotters were tested. The commercially available pre-spotters were (B) Zout™, (C) Safeway Prewash™, (D) Shout™, and (E) Spray 'n Wash™. The PEO concentration added to each pre-spotter was varied from 0.00%, 0.01%, 0.03% and 0.10%. The five samples containing varying amounts of PEO were sprayed into the beam of the Malvern Spraytec Laser System from a distance of 12 cm using five nozzles from Saint-Gobain Calmar (TS-800-1, TS-800-2, TS-800-3, TS-800-4, and TS-800-5). The results on particle size distribution are shown in Table 11 below where the values given are micrometers.

TABLE 11

Particle Size of Liquid Prespotter Sprayed into Beam of Malvern Spraytec Laser System

| Product | Polymer (PEO) concentration | | | |
|---|---|---|---|---|
| | 0.00% $D_{v10}$ 50 90 | 0.01% $D_{v10}$ 50 90 | 0.03% $D_{v10}$ 50 90 | 0.10% $D_{v10}$ 50 90 |
| Nozzle TS-800-1 | | | | |
| B | 62, 783, 959 | 607, 881, 980 | 208, 879, 960 | 282, 844, 967 |
| C | 602, 737, 927 | 329, 895, 981 | 714, 877, 976 | 822, 916, 983 |
| D | 348, 598, 866 | 272, 797, 968 | 500, 839, 969 | 501, 853, 972 |
| E | 493, 645, 912 | 282, 590, 882 | 665, 900, 980 | 526, 847, 971 |
| G | 106, 250, 454 | 507, 862, 973 | 565, 874, 975 | 683, 888, 978 |
| Nozzle TS-00-2 | | | | |
| B | 297, 837, 971 | 617, 889, 980 | 218, 770, 960 | 216, 893, 979 |
| C | 567, 711, 935 | 268, 893, 980 | 683, 881, 881 | 836, 921, 984 |
| D | 104, 303, 557 | 249, 686, 958 | 484, 831, 966 | 476, 806, 934 |
| E | 350, 536, 839 | 265, 616, 905 | 684, 895, 979 | 546, 861, 968 |
| G | 89, 225, 412 | 398, 788, 957 | 604, 894, 979 | 589, 855, 963 |
| Nozzle TS-800-3 | | | | |
| B | 463, 896, 980 | 650, 923, 985 | 298, 893, 979 | 360, 889, 979 |
| C | 529, 865, 969 | 515, 903, 981 | 687, 886, 978 | 838, 923, 985 |
| D | 270, 652, 895 | 270, 759, 966 | 457, 841, 969 | 482, 833, 967 |
| E | 542, 784, 945 | 261, 600, 909 | 561, 878, 976 | 601, 882, 977 |
| G | 230, 579, 840 | 412, 771, 945 | 642, 905, 981 | 605, 861, 960 |
| Nozzle TS-800-4 | | | | |
| B | 368, 846, 972 | 489, 896, 981 | 268, 819, 963 | 362, 887, 978 |
| C | 536, 710, 922 | 277, 892, 981 | 678, 872, 975 | 834, 918, 984 |
| D | 204, 458, 748 | 272, 685, 960 | 493, 843, 970 | 557, 849, 970 |
| E | 364, 574, 814 | 320, 656, 898 | 637, 899, 980 | 487, 825, 946 |
| G | 156, 389, 660 | 370, 757, 945 | 703, 909, 982 | 691, 894, 979 |
| Nozzle TS800-5 | | | | |
| B | 399, 846, 966 | 447, 904, 982 | 333, 735, 925 | 397, 819, 959 |
| C | 502, 676, 911 | 205, 877, 978 | 565, 845, 969 | 826, 917, 984 |
| D | 193, 435, 789 | 276, 711, 962 | 424, 812, 963 | 560, 856, 972 |
| E | 275, 499, 863 | 286, 620, 902 | 533, 851, 970 | 559, 858, 973 |
| G | 113, 315, 676 | 594, 837, 964 | 722, 910, 982 | 669, 909, 982 |

Table 11 demonstrates that the addition of polymer results in significantly larger droplet sizes, and generally more similar particle size distributions for all products and nozzle types as compared to the particle size distributions for the products and nozzle types without polymer. The similar particle size distributions are particularly evident for $D_{v50}$ and $D_{v90}$ values. For most of the products, the addition of polymer increased the $D_{v10}$ values, which suggests a reduction in aerosols.

The fluid properties of the pre-spotters were measured for reference, and for correlation to particle size distribution results. Table 12 lists the surface tension and shear viscosity values for products B through G.

TABLE 12

Surface Tension & Viscosity of Laundry Prespotters

| Product | Surface tension N/m | Fluid Class | Viscosity Centipoises | Flow Behavior Index |
|---|---|---|---|---|
| B | 0.0344 | Newtonian | 32.2 | 1 |
| C | 0.0345 | Newtonian | 5.4 | 1 |
| D | 0.0357 | Pseudoplastic | 747† | 0.44 |
| E | 0.0332 | Pseudoplastic | 153† | 0.62 |
| G | 0.0335 | Pseudoplastic | 718† | 0.49 |

†Apparent viscosity

The elongational viscosity was determined for the generic prespotter and a commercially available liquid laundry detergent, without polymer and with increasing amounts of polymer. Using the method described by H. Zhu, et.al. in "Effects of Polymer Composition and Viscosity on Droplet Size of Recirculated Spray Solutions", J. Agric. Eng. Res. (1997) 67, 35-45, the elongational flow times were measured for samples of the generic spray prespotter and locally purchased liquid laundry detergent with increasing levels of polyethylene oxide (PEO). The method comprises delivering 25 mL from a pipette through five (5) packed 100 mesh screens at the bottom exit and measuring the flow time. The flow time is an indirect measurement of elongational viscosity.

Figure 2:
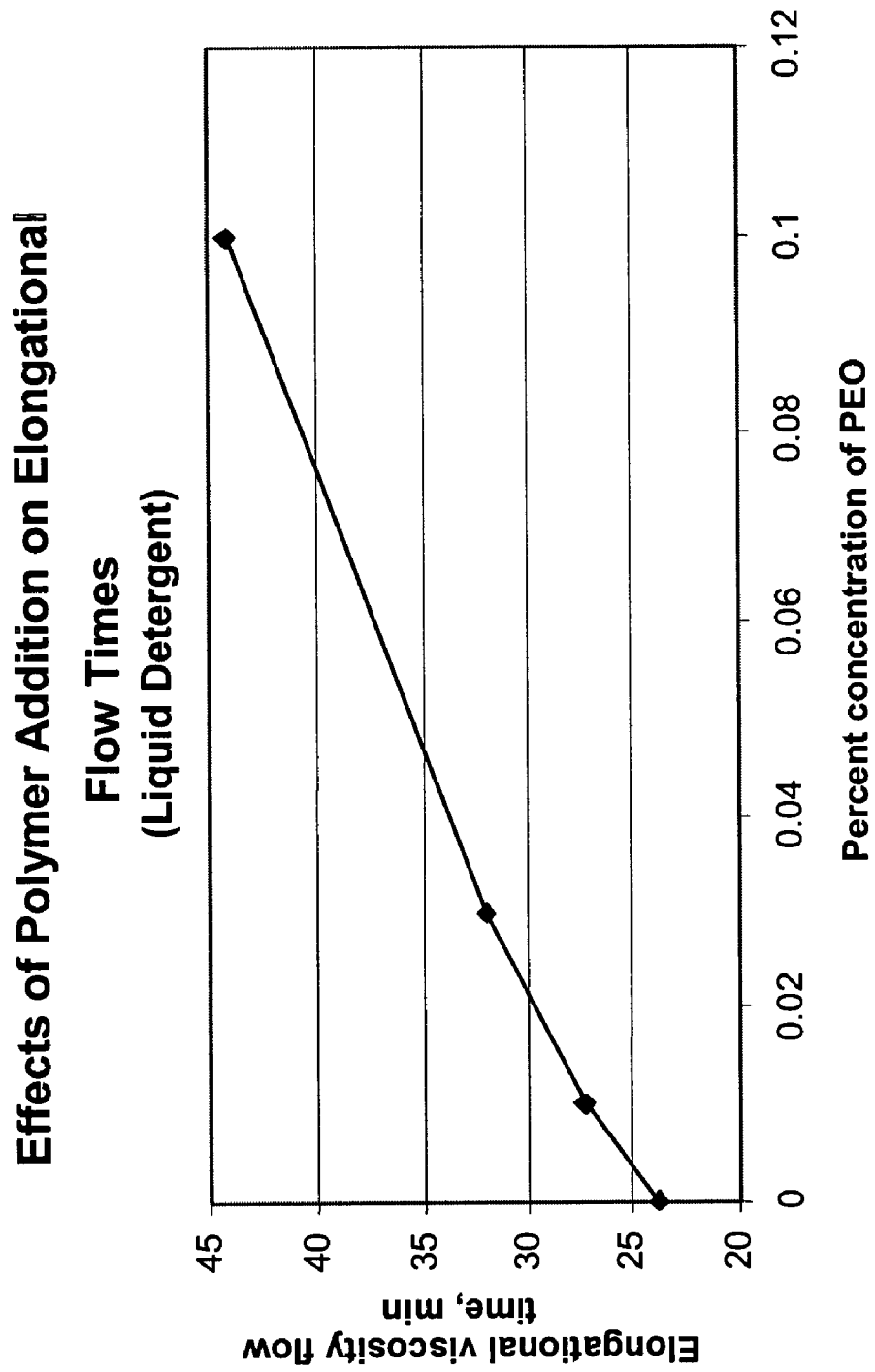
FIG. 2 is a graph showing the effects of polymer addition on elongational viscosity for a commercially available liquid detergent formulation.

As shown in FIGS. 1 and 2, the elongational flow times of the prespotter and liquid detergent increased as the polymer level increased. The increase in flow times correlates to an increase in elongational viscosity. The increasing elongational flow values of the prespotter correlate to the increasing $DV_{50}$ values of the prespotter in Table 11.

EXAMPLE 6

Mass Transfer Studies

Studies were conducted to measure the transfer of droplets during a simulated spray or splash event to determine the relationship between droplet size and actual airborne transport of aerosols during the application of pre-spotter (see Table 5) to fabric. Mass transfer is the movement of sprayed liquid from a point at the source of the spray to a point of eventual deposition of the spray. Mass transfer includes both movement of the sprayed liquid within ambient air and movement to a deposition surface.

The tracer, fluoroscein, 0.01%, was added to a sample of the generic pre-spotter (G) instead of enzyme. Fluoroscein does not affect the particle size distribution of the products. Fluoroscein can be readily measured with high sensitivity, and is therefore a reasonable surrogate for enzyme in this application. A Turner 450 Fluorometer (Model 45F00-05 from Barnstead/Thermolyne Corporation, Dubuque, Iowa) was used to detect and measure any fluoroscein reaching an aerosol collection site. The fluorometer was equipped with a narrow band excitation filter (490 nm) and a 520 nm emission filter.

An air sampler with an 11 cm² diameter glass fiber filter was used to collect any aerosol particles containing the fluoroscein tracer at the collection site. The air sampler was placed downstream at the end of the wind tunnel to collect the finest particles of the distribution spectrum, and the pre-spotter was dispensed from commercial hand pumped spray nozzles placed at the upstream end of the wind tunnel. The product sample was sprayed from the top upwind end of the tunnel onto the center of the floor of the tunnel, and the floor was covered with cheesecloth to minimize rebound and provide a reservoir for any excess material. The location was 1.07 m from the spray site and 1.33 m from the downwind end of the tunnel. The wind tunnel fan and air sampler were operated at 7.0 m/s and 1.7 m/s, respectively. The air sampler and filter were mounted within the front of the beam of the Malvern Spraytec Laser.

Following collection, the filter was removed from the sampler and placed in a 60 ml. container to which 30.0 grams of distilled water was added. The container was closed and shaken for 2 hours to extract the fluoroscein from the filter paper. A 10 ml. sample of the extracted solution was decanted into a centrifuge tube and centrifuged for 6 minutes at 4100 rpm. The supernatant was transferred by pipette to a fluorometer sample tube.

Two measurements were made for each nozzle TS-800-1 through TS-800-5 with and without 0.01% PEO in the samples. Both particle size distribution of particles reaching the air sampler and the mass of particles reaching the air sampler were measured. Results shown in Table 13 demonstrate significantly reduced recovery of fluoroscein in the samples containing 0.01% PEO polymer, which indicates a significant reduction of the total mass of aerosols reaching the sampler. The results further demonstrate that the particles that reached the air sampler were less than 60 microns in size.

TABLE 13

Mass Transfer

| Nozzle | PEO % | Fluoroscein Mean Recovery ppb[†] | Generic formulation on air sampler, g[‡] | Mass % of 30 squirts (30 g) reaching air sampler[‡] | Reduction in fines with polymer %[‡] |
|---|---|---|---|---|---|
| TS-800-1 | 0.00 | 341.5 | 0.4714 | 1.57 | — |
| TS-800-1 | 0.01 | 22.0 | 0.0491 | 0.16 | 93.9 |
| TS-800-2 | 0.00 | 680.9 | 0.1615 | 0.54 | — |
| TS-800-2 | 0.01 | 21.7 | 0.0161 | 0.05 | 94.4 |
| TS-800-3 | 0.00 | 89.5 | 0.0776 | 0.26 | — |
| TS-800-3 | 0.01 | 13.1 | 0.0426 | 0.14 | 86.3 |
| TS-800-4 | 0.00 | 460.2 | 0.4520 | 1.51 | — |
| TS-800-4 | 0.01 | 23.8 | 0.0562 | 0.19 | 94.4 |
| TS-800-5 | 0.00 | 497.1 | 0.3126 | 1.04 | — |
| TS-800-5 | 0.01 | 33.9 | 0.0321 | 0.11 | 90.7 |

[†]Contained in 30 g of air sampler filter extract.
[‡]Particles reaching air sampler are less than 60 microns A correlation between $D_{v10}$ values and downwind transport of aerosols was found. Addition of polymer reduced mass transfer by about 84-96%. Mitigation of aerosol generation was achieved.

EXAMPLE 7

Droplet Size Mass Transfer Studies with Rebound

Mass transfer is dependent on particle size, as shown in Example 6, and using polymers to increase the size of the particles predictably resulted in reduced or eliminated transfer of large particles to the detector. The mass transfer studies were repeated to determine the effect of the polymer on droplet size following rebound from a surface.

Spray experiments were conducted in a wind tunnel using an automatic dispersing stand. The dispersing stand was constructed to hold the spray bottle in a fixed position while mechanically depressing the bottle trigger in a repetitive fashion. The Generic Prespotter (Table 5, containing 0.01% Fluorescein tracer) with varying levels of polyethylene oxide (PEO) was sprayed 30 times (using two different Saint-Gobain Calmar TS-800-1 and TS-800-3 nozzles) onto various surfaces (glass, cotton, polyester/cotton) at the upwind end of the wind tunnel. The spray bottle nozzle was fixed in position with respect to the surface (2.75 inches vertically above the surface and at a 45 degree angle to the surface). The floor of the wind tunnel was covered with layers of cheesecloth to eliminate rebound from this surface. The air sampler and Malvern Spraytec Particle Size Analyzer were mounted at the downwind end of the wind tunnel. The wind tunnel and air sampler were operating at 7.0 m/s and 1.7 m/s respectively. Experiments were run with surfaces in place and with the surfaces removed. When the surfaces are removed, the entire spray hits the cheesecloth (no rebound) on the floor of the wind tunnel. The results of these experiments are shown in Table 14. When the surfaces were in place, the droplets reaching the air sampler were the result of both the initial spray and surface rebound. However when the surfaces were removed, the droplets reaching the air sampler were the result only of the initial spray.

TABLE 14

Mass Transfer

| Nozzle | PEO % | Rebound Surface | Prespotter Mass on Air Filter (mg) | % Reduction in Mass with PEO | Particle Size at Air Sampler |
|---|---|---|---|---|---|
| TS-800-1 | 0.00 | None | 45 | | |
| TS-800-3 | 0.00 | None | 11.1 | | ND* |

TABLE 14-continued

Mass Transfer

| Nozzle | PEO % | Rebound Surface | Prespotter Mass on Air Filter (mg) | % Reduction in Mass with PEO | Particle Size at Air Sampler |
|---|---|---|---|---|---|
| TS-800-1 | 0.00 | Glass | 113.5 | | |
| TS-800-3 | 0.00 | Glass | 166 | | ND |
| TS-800-1 | 0.00 | Cotton | 69.6 | | |
| TS-800-3 | 0.00 | Cotton | 91.9 | | ND |
| TS-800-1 | 0.00 | Polyester/Cotton | 82.6 | | |
| TS-800-3 | 0.00 | Polyester/Cotton | 112.5 | | ND |
| TS-800-1 | 0.01 | None | 3.8 | 92 | ND |
| TS-800-3 | 0.01 | None | 5.9 | 47 | ND |
| TS-800-1 | 0.01 | Glass | 8.6 | 95 | ND |
| TS-800-3 | 0.01 | Glass | 6.9 | 94 | ND |
| TS-800-1 | 0.01 | Cotton | 3.3 | 96 | ND |
| TS-800-3 | 0.01 | Cotton | 3.8 | 95 | ND |
| TS-800-1 | 0.01 | Polyester/Cotton | 2.7 | 98 | ND |
| TS-800-3 | 0.01 | Polyester/Cotton | 5.1 | 94 | ND |
| TS-800-3 | 0.03 | None | 1.8 | 84 | ND |
| TS-800-3 | 0.03 | Glass | 0.8 | 99 | ND |

*Above Malvern size detection threshold.

The results in Table 14 show that, without polymer and with no rebound surface, 45 mg of generic prespotter reached the air sampler from the TS-800-1 nozzle and 11.1 mg reached the air sampler from the TS-800-3 nozzle. Nozzle TS-800-3 produced more of a jet-like spray with fewer droplets in the less than 60 μm range as compared to the TS-800-1 nozzle which produced only droplets less than 60 microns at the air sampler. All droplets were produced as a result of the initial spray dispersion from the nozzle in the absence of a rebound surface.

When a rebound surface was in place, droplets that reached the air sampler had a bimodal size distribution (droplets less than 60 μm from the initial spray and droplets in the 60-300 μm range from the rebound event for the TS800-1 nozzle). As the rebound surface was changed from cotton to polyester/cotton (65/35) to glass thereby increasing surface hardness, the bimodal size distribution shifted from being more heavily weighted in the less than 60 μm size fraction to being more heavily weighted in the 60-300 μm size fraction. The droplets were produced as a result of the initial spray and the rebound event respectively.

As the surface was changed from no surface to cotton to polyester/cotton to glass, the mass of Generic Prespotter reaching the air sampler from the TS-88-1 nozzle increased from 45 mg to 91.9 mg to 112.5 mg to 166 mg. These shifts in mass were in qualitative agreement with the shifts in the bimodal distribution.

For the TS-800-3 nozzle as the surface was changed from no surface to cotton to polyester/cotton to glass, the mass of Generic Prespotter reaching the air sampler increased from 11.1 mg to 69.6 mg to 82.6 mg to 113.5 mg. No droplets were detected by the Malvern Spraytec Particle Size Analyzer from the TS-800-3 nozzle because the particle size was above the threshold of the instrument.

When 0.01% PEO was added to the Generic Prespotter, the mass reaching the air sampler from the TS-800-1 nozzle was reduced by 92% (no rebound surface), 96% (cotton), 98% (polyester/cotton), and 95% (glass), and no droplets were detected by the Malvern Spraytec Particle Size Analyzer. The mass of Generic Prespotter reaching the air sampler from the TS-800-3 nozzle was reduced by 47% (No rebound surface), 95% (cotton), 94% (polyester/cotton), and 94% (glass). No droplets were detected by the Malvern.

Two additional tests were conducted with the TS-800-3 nozzle, which produces a jet-like spray, using 0.03% PEO polymer with no rebound surface and for a glass rebound surface. With no rebound surface only 1.8 mg of Generic Prespotter reached the air sampler as compared to 11.1 mg for the sample containing 0.01% PEO. For the glass surface only 0.8 mg of the Generic Prespotter reached the air sampler as compared to 6.9 mg for the sample containing 0.01% PEO. No droplets are detected by the Malvern. It is noteworthy that even with the most jet-like spray pattern from the Nozzle TS-800-3, as compared to the other TS-800 series nozzles which produced more dispersed spray patterns, and the highest concentration of PEO to enhance the jet, the particle mass that was rebounded from the glass surface was essentially zero.

EXAMPLE 8

Polymer Formulation Stability

To determine the stability of the polymer under storage conditions, initial elongational viscosity values were determined for polymer added to Generic Prespotter and to commercial prespotter E containing 0.01, 0.03 and 0.1% PEO. Elongational viscosity values were repeated following storage of the spiked samples at room temperature for 4.5 months. Elongational viscosity values were not affected by storage of the polymer in the Commercial prespotter E, and elongational viscosity values were slightly decreased by storage of the polymer in Generic Prespotter.

One skilled in the art is aware of many variations of the methods described above for making the high molecular weight polymer anti-misting compositions according to the invention.

What is claimed is:

1. A reduced aerosol generating personal care or cleaning product comprising
    a) 0.0001% to about 1.5% of high molecular weight polyethylene oxide by weight;
    b) an enzyme; c) an enzyme protecting agent and d) one or more personal care or cleaning product components, wherein the personal care or cleaning product is a liquid, wherein said polyethylene oxide is an anti-misting agent and the $D_{v50}$ of the personal care or cleaning product is increased by 10%-200% over a corresponding personal care or cleaning product, wherein the corresponding personal care or cleaning product comprises the enzyme, the enzyme protecting agent and the one or more personal care or cleaning product components but does not comprise the high molecular weight polyethylene oxide.

2. The reduced aerosol generating product of claim 1, wherein said polyethylene oxide comprises a molecular weight from about $0.8 \times 10^6$ to $4 \times 10^6$.

3. The reduced aerosol generating product of claim 1, wherein the product is a personal care product selected from the group consisting of a shower or bath gel, a facial cleaner, a lotion, a hair shampoo, and a liquid soap.

4. The reduced aerosol generating product of claim 1 wherein the product is a cleaning product selected from the group consisting of a detergent, a hard surface cleaner, a prespotting cleaner, and a carpet cleaner.

5. The reduced aerosol generating product of claim 1, wherein the $Dv_{50}$ of the formulated product is in the range of 55 μm 900 μm.

6. The reduced aerosol generating product of claim 1, wherein the $Dv_{50}$ of the formulated product is greater than 60 μm.

7. The reduced aerosol generating product of claim 1, wherein the $Dv_{50}$ of the formulated product is greater than 100 μm.

8. The reduced aerosol generating product of claim 4, wherein the enzyme is selected from the group consisting of a protease, an amylase, a cellulase, an oxidase, and a lipase.

9. A method of reducing aerosol generation from a personal care or cleaning product comprising combining said product with an aqueous composition comprising a high molecular weight polyethylene oxide having a molecular weight from about $0.8\times10^6$ to $4\times10^6$, an enzyme, and an enzyme protecting agent, thereby obtaining a modified product, wherein said modified product is a liquid, wherein the $Dv_{50}$ of said modified product is increased by 10% to 200% over the $Dv_{50}$ of a corresponding personal care or cleaning product, wherein the corresponding personal care or cleaning product comprises the enzyme and the enzyme protecting agent but does not comprise the high molecular weight polyethylene oxide.

10. The method according to claim 9, wherein the enzyme and the polyethylene oxide are added together to the personal care or cleaning product during the combining step.

11. The method according to claim 9, wherein the modified product comprises about 0.0001% to about 5.0% of the enzyme by weight.

12. The method according to claim 9, wherein the modified product comprises from 0.0001% to about 1.5% of the polyethylene oxide by weight.

13. A reduced aerosol generating modified product produced by the method of claim 9.

14. A method of decreasing enzyme exposure from a personal care or cleaning product comprising combining a personal care or cleaning product which includes one or more enzymes with an aqueous composition comprising a polyethylene oxide polymer having a molecular weight of about $0.8\times10^6$ to $4.0\times10^6$, wherein said polymer is an anti-misting agent, and an enzyme protecting agent, wherein the personal care or cleaning product is a liquid.

15. The method according to claim 14, wherein the product is a personal care product selected from the group consisting of a shower or bath gel, a facial cleaner, a lotion, a hair shampoo, and a liquid soap.

16. The method according to claim 14, wherein the cleaning product is selected from the group consisting of a detergent, a hard surface cleaner, a pre-spotting cleaner, and a carpet cleaner.

17. The method according to claim 14, wherein the enzyme is a protease.

18. An aqueous anti-misting enzyme composition comprising a) from about $1\times10^{-4}$ to 1.5 wt % of high molecular weight polyethylene oxide;

b) from about $1\times10^{-4}$ to 10 wt % of an effective amount of one or more enzymes; and c) an enzyme protecting agent, wherein said anti-misting composition is a liquid.

19. The anti-misting enzyme composition of claim 18, wherein said polyethylene oxide comprises a molecular weight from about $0.8\times10^6$ to $4.0\times10^6$.

20. A personal care product comprising the anti-misting enzyme composition of claim 18, wherein the personal care product is a liquid.

21. The personal care product of claim 20, wherein the personal care product is selected from the group consisting of a shower or bath gel, a facial cleaner, a lotion, a hair shampoo, and a liquid soap.

22. A cleaning product comprising the anti-misting product of claim 18, wherein the cleaning product is a liquid.

23. The cleaning product of claim 22, wherein the cleaning product is selected from the group consisting of a detergent, a hard surface cleaner, a pre-spotting cleaner, and a carpet cleaner.

24. The anti-misting enzyme composition of claim 18 wherein the enzyme protecting agent is propylene glycol.

25. A method for producing a reduced aerosol generating personal care or cleaning product, said method comprising combining 0.0001% to about 5.0% of high molecular weight polyethylene oxide by weight with an enzyme, an enzyme protecting agent, and one or more personal care or cleaning product components to obtain a personal care or cleaning product having reduced aerosol generation in comparison with a corresponding personal care or cleaning product, wherein the corresponding product comprises the enzyme, the enzyme protecting agent and the one or more personal care or cleaning product components but does not comprise said polyethylene oxide, wherein said high molecular weight polyethylene oxide comprises a molecular weight of about $0.8\times10^6$ to about $4\times10^6$, wherein the reduced aerosol generating personal care or cleaning product is a liquid, and wherein the reduced aerosol generation reduces enzyme exposure in comparison to said corresponding product.

26. The method of claim 25, wherein the enzyme protecting agent is a water miscible nonsolvent, and wherein the method further comprises dispersing the polyethylene oxide in the water miscible nonsolvent prior to combining the polyethylene oxide with the enzyme.

27. The method of claim 25 wherein the combining is conducted at about 35° C.

28. A method of reducing aerosol generation of an enzyme-containing personal care or cleaning product comprising combining said product with a composition comprising an enzyme protecting agent and a polyethylene oxide polymer having a molecular weight from about $0.8\times10^6$ to about $4\times10^6$ to obtain a modified enzyme-containing personal care or cleaning product wherein the concentration of the polymer is from about 0.0001% to about 1.5% of the modified product by weight, wherein the modified product is a liquid, and wherein the $Dy_{50}$ of the modified product increases by 10%-200% in comparison with a corresponding enzyme-containing personal care or cleaning product, wherein the corresponding personal care or cleaning product comprises the enzyme and the enzyme protecting agent but does not comprise the polyethylene oxide polymer.

29. A shower gel comprising a polyethylene oxide polymer wherein said polymer has a molecular weight from about $0.8\times10^6$ to $4\times10^6$ and comprises from about 0.0001% to about 1.5% of the shower gel by weight; a protease comprising about 0.0001% to about 10% of the shower gel by weight; an enzyme protecting agent; and one or more further personal care product ingredients wherein said shower gel has a $Dv_{50}$ that is 10-200% greater than a corresponding shower gel lacking the high molecular weight polyethylene oxide polymer.

30. A method according to claim 9, wherein said enzyme is incorporated into said formulated product separately from the high molecular weight polyethylene oxide aqueous composition.

31. A method according to claim 1, wherein the enzyme protecting agent is propylene glycol.

32. A method according to claim 9, wherein the enzyme protecting agent is propylene glycol.

33. A method according to claim 14, wherein the enzyme protecting agent is propylene glycol.

34. A method according to claim 25, wherein the enzyme protecting agent is propylene glycol.

35. A method according to claim 28, wherein the enzyme protecting agent is propylene glycol.

* * * * *